United States Patent
Lange

(10) Patent No.: US 6,603,541 B2
(45) Date of Patent: Aug. 5, 2003

(54) WAFER INSPECTION USING OPTIMIZED GEOMETRY

(75) Inventor: Steven R. Lange, Alamo, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 09/934,954

(22) Filed: Aug. 21, 2001

(65) Prior Publication Data

US 2003/0086082 A1 May 8, 2003

Related U.S. Application Data

(60) Provisional application No. 60/302,222, filed on Jun. 28, 2001.

(51) Int. Cl.[7] ............................................. G01N 21/00
(52) U.S. Cl. ................................. 356/237.2; 356/237.3
(58) Field of Search ........................ 356/237.1–237.5; 250/571, 559.41; 382/141, 144, 145

(56) References Cited

U.S. PATENT DOCUMENTS

| 4,710,642 | A |   | 12/1987 | McNeil ...................... 250/571 |
| 5,241,369 | A |   | 8/1993 | McNeil et al. ............... 356/445 |
| 5,805,278 | A | * | 9/1998 | Danko ................... 250/559.41 |
| 5,982,921 | A |   | 11/1999 | Alumot et al. .............. 382/145 |
| 6,137,570 | A |   | 10/2000 | Chuang et al. |
| 6,404,498 | B1 | * | 6/2002 | Maeda et al. ............ 356/237.5 |
| 6,411,377 | B1 | * | 6/2002 | Noguchi et al. ......... 356/237.4 |
| 6,496,256 | B1 |   | 12/2002 | Eytan et al. |

FOREIGN PATENT DOCUMENTS

WO  WO 00/02037  1/2000

* cited by examiner

Primary Examiner—Michael P. Stafira
(74) Attorney, Agent, or Firm—Beyer Weaver & Thomas LLP

(57) ABSTRACT

The present invention pertains to an optical inspection system capable of obtaining very high signal-to-noise ratio data and that is capable of high speed scanning rates. The ability to obtain high signal-to-noise data is obtained by selecting parts of the scattering hemisphere where signal from a defect is high and noise due to scattering from wafers structures is low. One embodiment of the optical inspection system includes a set of lenses used to form an image of the inspected specimen at a Fourier plane with telecentric-in-object space imaging. Another embodiment of the optical inspection system includes a substantially hemispherical shaped mirror system that provides a large collection numerical aperture that allows for the collection of substantially all of the hemisphere of scattered light from an inspected specimen. The present invention also discloses techniques for enhancing the signal-to-noise ratio of image data received from the optical inspection system.

23 Claims, 7 Drawing Sheets

WAFER INSPECTION USING OPTIMIZED GEOMETRY

This application claims priority of U.S. Provisional Patent Application No. 60/302,222, filed Jun. 28, 2001 entitled "Wafer Inspection Using Optimized Collection Geometry," which is hereby incorporated by reference.

FIELD OF THE INVENTION

The present invention relates generally to optical inspection systems, and more specifically to optical inspection systems for obtaining data having very high signal-to-noise ratios.

BACKGROUND OF THE INVENTION

The present invention relates generally to methods of inspecting patterned and unpatterned semiconductor wafers for defect acquisition and defect classification. One known method of inspecting wafers involves illuminating a relatively small spot on a wafer using a light source such as a laser beam. This small spot of light is scanned over the wafer using either raster or spiral scanning until the surface of the wafer to be inspected has been covered. The light scatters from the wafer structures into a hemisphere in various directions with intensities depending upon the structure on the wafer's surface and any defects on the surface. The objective is to locate the defects on the wafer in the presence of scatter from both the defect and the intentional structures on the wafer's surface associated with the device (e.g., computer processor or memory chip) being fabricated on the wafer. The scatter from the structures can be considered noise to the signal that is the scatter from the defect. The scattered light is commonly detected by a fixed number of detectors in fixed positions about the hemisphere.

In order to detect a defect, the signal-to-noise ratio of the collected scattered light must be sufficiently high. To obtain the most accurate defect analysis, it is desirable to locate the direction of the scattered light where the signal-to-noise ratio is the highest. The optimal region for the collection of scattered light can be anywhere on the hemisphere. By finding the optimum location in the hemisphere, the signal-to-noise ratios can easily be over 50 times greater than with fixed collection locations within the hemisphere. Therefore, to obtain the optimal signal to noise ratio, it is desirable to sample the entire hemisphere. Practically, it is not cost effective or easy to construct a complete hemisphere of detectors. Therefore, in current applications, a limited number of detectors are placed in what are hoped to be the optimal positions to obtain high signal-to-noise signals.

Unfortunately, in simulations of light scatter from relatively complicated structures with defects, the maximum signal-to-noise ratio location in the hemisphere can be considerably higher than signal-to-noise ratio from the fixed collector positions of current inspection systems. One option to compensate for the collector positions of the current inspection systems is to collect scattered light over a larger area of the hemisphere using larger detectors. This option may not be completely satisfactory since larger detectors collect more noise in addition to the increased signal collection. Thus, larger detectors do not necessarily improve the ratio of signal-to-noise. Another option is to use detectors that can be moved about the hemisphere to the locations of the highest signal-to-noise ratio. This option is not very viable, however, since the optimal location within the hemisphere changes as a function of the structure of the wafer and the types of defects, thereby requiring the frequent repositioning of the detectors. In light of the foregoing, it is desirable to have the ability to detect scattered light in a majority of the hemisphere of scattered light in order to obtain the highest possible signal-to-noise ratio for detecting defects as the wafer's structure changes in the presence of a scanning spot over the wafer's surface.

BRIEF SUMMARY OF THE INVENTION

The present invention pertains to an optical inspection system capable of obtaining very high signal-to-noise ratio data and that is capable of high speed scanning rates so the defects are found quickly. The ability to obtain high signal-to-noise data is contributed to various aspects of the present invention. One aspect of the optical inspection system that contributes to a high signal-to-noise ratio is a set of lenses used to form an image of the inspected specimen at a Fourier plane. Another aspect of the optical inspection system is a substantially hemispherical shaped mirror system that provides a large collection numerical aperture that allows for the collection of substantially all of the hemisphere of scattered light from an inspected specimen. Several embodiments of the present invention also disclose techniques for enhancing the signal-to-noise ratio of image data received from the optical inspection system. The signals collected by the inspection system can help identify and classify the defect types according to the distribution of the light scattered from the wafer. This is possible since the angular distribution of light is representative of the defect types.

One aspect of the present invention pertains to an optical inspection system that includes a specimen to be analyzed, a light source, a set of optical lenses and a plurality of detectors. The light source transmits a light beam incident upon the surface of the specimen, which causes light rays to scatter from the surface of the specimen. The set of optical lenses is job positioned to receive the light rays scattering from the specimen and is configured to transmit the scattered light rays into a Fourier plane, whereby a map of the angular distribution of light scattered from the surface of the specimen is created at the Fourier plane. The plurality of detectors are placed in the Fourier plane to detect the scattered light rays, whereby the surface features of the specimen can be determined from the collected scattered light.

In an alternative embodiment of the inspection system, a substantially hemispherical mirror is placed over an area of the specimen to be inspected, the mirror being configured to collected and then direct the scattered light from the specimen towards the set of optical lenses. The mirror is capable of collecting and directing light rays that scatter into substantially a full hemisphere from the surface of the specimen.

Another aspect of the present invention relates to a method for detecting defects on a specimen using the optical inspection system. The method includes irradiating a spot on the specimen with a light source, the light source causing light rays to scatter from the surface of the specimen. Then detecting the image of the scattered light rays at a Fourier plane, the Fourier plane created by a set of Fourier plane forming lenses within the optical inspection system. Then multiplying the signal value for each discrete portion of the irradiated spot by a respective vector value to obtain a respective adjusted signal value. The respective vector values cause the respective adjusted signal value to increase if the respective signal value is associated with a high defect signal. The respective vector values also cause the respective adjusted signal value to decrease if the respective signal value is associated with a noise defect signal. And then, evaluating a sum total of the respective adjusted signal values for the irradiated spot to determine whether a defect exists within the irradiated spot on the specimen.

These and other features and advantages of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

The present invention pertains to an optical inspection system that is capable of obtaining both very high signal-to-noise ratio data and capable of high speed scanning rates. The ability to obtain high signal-to-noise data is contributed to by various aspects of the present invention. One aspect of the optical inspection system that contributes to a high signal-to-noise ratio is the set of lenses used to form a Fourier representation of the inspected specimen at a Fourier plane. Another aspect of the optical inspection system is a substantially hemispherical shaped mirror system that provides a large collection numerical aperture. Several embodiments of the present invention also disclose techniques for enhancing the signal-to-noise ratio of image data received from the optical inspection system.

Figure 1:
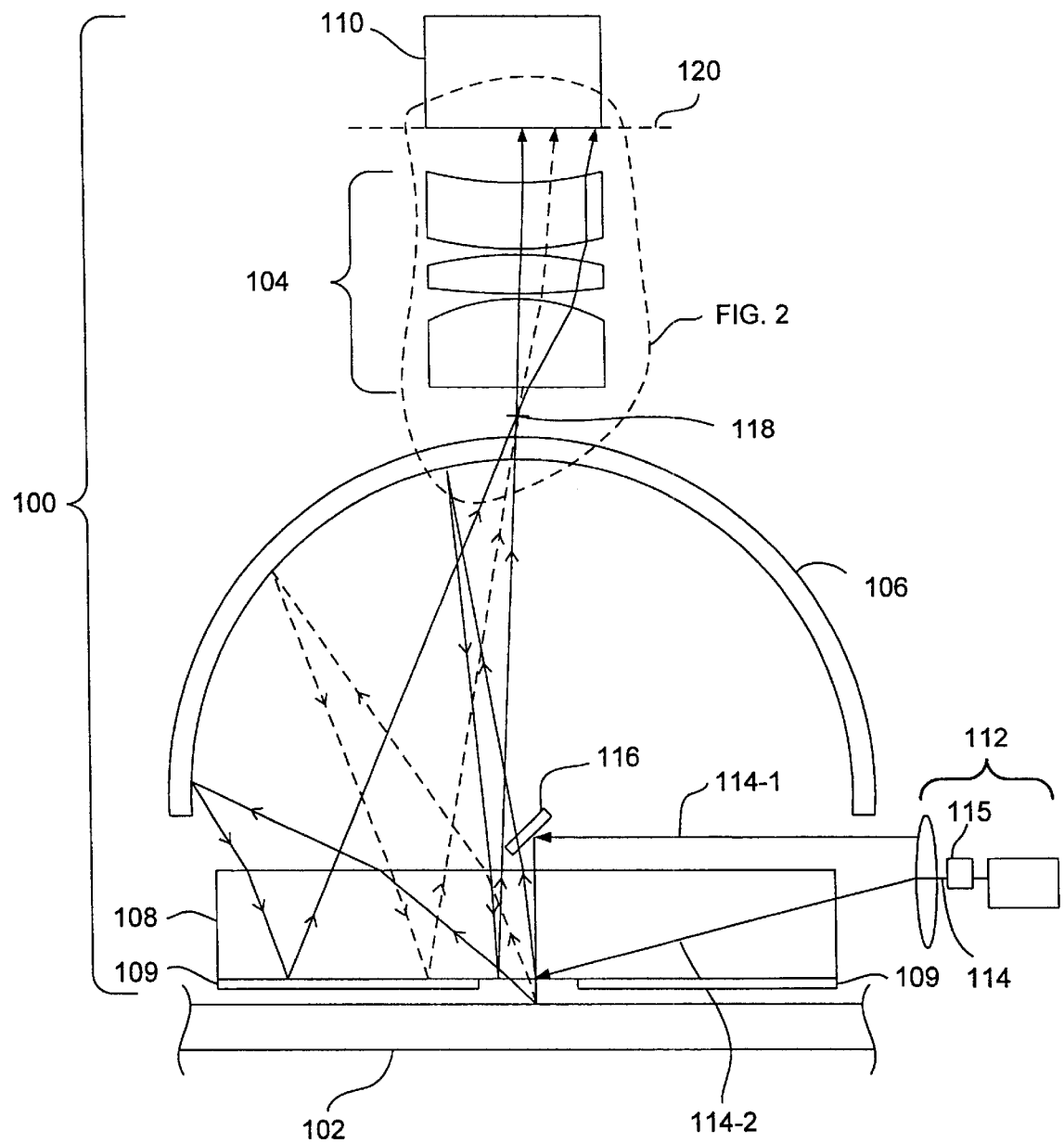
FIG. 1 illustrates a side plan, cross-sectional view of an optical inspection system according to one embodiment of the present invention.

FIG. 1 illustrates a side plan, cross-sectional view of an optical inspection system 100 according to one embodiment of the present invention. The optical inspection system 100 is shown in FIG. 1 while being used in one of the typical uses of inspecting a semiconductor wafer 102 for defects, such as contaminating particulates or an incorrectly formed circuit structure. In order for inspection system 100 to inspect the entire surface of wafer 102, the light source is scanned relative to the inspection system 100 using scanning device 115, which scans the light source in an inspecting swath equal to the field of view of the inspection system optics. The wafer is moved underneath the inspection system 100 such that the wafer 102 will be inspected in a raster scanned manner of swaths. Alternatively, the wafer can be rotated while the lens system 100 is shifted such that the surface of the wafer is completely scanned in a spiral pattern of swaths. In this case, the radial and angular coordinates of the image can be transformed to Cartesian coordinates for computational purposes and to eliminate spatially periodic structures on the wafer. Alternatively, the inspection system 100 can be moved relative to the wafer 102 or both the inspection system 100 and the wafer 102 can be moved relative to each other. Inspection system 100 can also be used to inspect specimens other than semiconductor wafers.

To describe the novel aspects of the present invention without unnecessary information, all of the structures of the inspection system 100 have not been illustrated. For instance, the protective housing that would support and protect the inspection system 100 has not been illustrated and will not be discussed.

Inspection system 100 includes a set of lenses that form a Fourier plane, referred to as the Fourier forming lenses 104, a hemispherical mirror 106, an optical plate element 108 with a mostly mirrored bottom 109, a detector 110, and a light source 112. The light source, typically a laser, 112 introduces a light beam 114 through a scanning device 115 so that the light beam 114 travels through an optical plate element 108 in order to illuminate a spot on the wafer 102. The NA of the light source, typically a laser beam, preferably has a low NA of approximately 0.01–0.05 such that the smaller dimension of the spot size of the light on the wafer 102 is about 10–50 um. It is noted that the spot size can vary depending upon the specific testing requirements of different specimens or inspection system configurations.

A brief explanation of the path taken by the light beam 114 and the resulting scattered light will be provided. As illustrated, the light beam 114 can be directed towards the wafer 102 in two manners. One manner directs the light beam 114 in a normal orientation with the optical plate element 108 such that a re-directing mirror 116 directs the light beam 114-1 towards the wafer 102. Another manner directs the light beam 112 in an oblique orientation such that light beam 114-2 travels through the optical plate element 108. After the light beam 114 reaches the wafer 102, light rays will scatter from the point of incidence into various directions of a hemisphere and at different intensities. As is required with most optical inspection systems, the light beam 114 is then directed out of the inspection system 100 by various mirror placements (not shown). More importantly, the scattered light rays bounce up from the wafer 102 and through the optical plate element 108. The scattered light then reflects off various points of the mirror 106 to be directed back into mirrored part 109 of the optical plate element 108, which then directs the scattered rays to a convergent point 118 near the vertex of the mirror 106. From the convergent point 118, the scattered rays pass through the Fourier forming lenses 104 and into a Fourier plane 120.

Detector 110 is positioned at the Fourier plane 120 in order to capture the scattered rays and form an image for defect detection purposes. As is appreciated by those of skill in the art, an illuminating light beam can be introduced into inspection system 100 in a variety of manners.

The hemispherical mirror 106 and the optical plate element 108 work together to give the inspection system 100 a high collection numerical aperture. In one embodiment of the inspection system 100, the collection numerical aperture (NA) is approximately 0.996. Given that the NA equals the sin of the half angle of collected scattered light, this embodiment collects approximately 170 degrees of the light that scatters from the wafer 102. This very large collection angle allows the inspection system 100 to gather scattered light from a large majority of the hemisphere into which light scatters off the wafer 102. Specifically, the inspection system can collect scattered light rays that have very large scattering angles, which refers to the rays that scatter in a direction near parallel to the surface of the wafer. Of course, the inspection system 100 can also collect rays that scatter in a more perpendicular direction with the wafer 102. In various embodiments of the inspection system 100, the size of the mirror 106 can be varied such that the collection NA is in the range of approximately 0.90–0.996. The capability to collect large angles of scattered light is an important feature since high ratios of defect signal to noise scatter can be maximized at almost any of the angles within a hemisphere. This feature of the inspection system 100 increases the capability of obtaining high signal-to-noise ratio data. By using detected signals from the optimal locations for signal-to-noise, the signal-to-noise ratios can be approximately in the range of 50–70 greater than fixed collector positions. As should be understood, the present invention allows detectors in a single plane to detect signals from a substantial portion of a hemisphere of scattered light. The present invention is therefore flexible since detectors need not be strategically placed in hemispherical positions about the inspected specimen.

The mirror 106 and optical plate element 108 direct the scattered light rays through various paths until they ultimately form an intermediate focus 118 located at or near a hole in the mirror 106. From the intermediate focus location 118, the scattered light rays proceed to the Fourier forming lenses 104. The mirror 106 and optical plate element 108 convert the large collection NA to a relatively small exit NA at the intermediate focus 118 of approximately 0.6–0.7. The size of the collection and exit NA can vary depending upon the requirements for a specific implementation of the inspection system 100.

The optical plate element 108 is an optical element which has a small transparent zone where the light from the light source reaches the wafer and the light scattered from the wafer passes through. The remaining part of the lower surface of the optical plate element 108 is reflective to allow the rays that reflect off the spherical mirror to reflect again off this reflective surface 109 and towards the intermediate focus 118 near the vertex of the hemispherical mirror 106.

The properties of the optical plate element 108 are preferably such that low amounts of light scatter from the surface and the bulk of the optical plate element 108. The flat plate can be formed from materials such as fused silica and high-quality optical glass and crystalline materials such as $CaF_2$. The diameter of the optical plate element 108 can vary between 50–100 mm. In one embodiment, the optical plate element 108 has a diameter of about 70-mm.

The Fourier forming lenses 104 receive the scattered light rays from the mirror 106 and optical plate element 108 combination and direct them towards a Fourier plane 120. The light rays form an image at the Fourier plane 120, which is detected by detector 110 in order to obtain information about the wafer 102. The Fourier forming lenses 104 include three separate optical lenses. In FIG. 1, the lenses are shown to be spherical in shape. However, as is commonly known, lenses used to form a Fourier plane can consist of a variety of lens types and prescriptions and the number of lenses used can vary. In preferred embodiments of the inspection system 100, the detection solid angle resolution should have a numerical aperture of about 0.05. Therefore, the angular resolution of the Fourier transform lens need not be extremely high with a minimum of 18 detection elements across the Fourier plane.

The inspection system 100 is telecentric in object space and the lens system 100 also has a field of view of about 2 mm. The inspection system 100 therefore has a Fourier plane 120 that is telecentric in object space. Telecentricity allow rays that leave the surface of the wafer 102 at a given angle to converge on the same spot at the Fourier plane 120. This is important because knowing the angle at which light scatters from the wafer 102 provides information about defects on the wafer 102, which will be invariant across the field of view in a telecentric system. The telecentric aspect of the inspection system 100 facilitates more efficient defect analysis because the light source can be scanned over the specimen surface without regard that the light source will change the signal or noise of a specific wafer structure regardless of where the structure exists within the field of view of the optical system. Even though the light source is being scanned, scattered light with specific angles will still converge upon the same point on the Fourier plane 120. A substantially uniform image of the wafer surface and its defects can be obtained for each of the discrete areas scanned by the light source, which allows for simpler analysis techniques. Additionally, scanning of the light source allows for faster inspection of specimens and production cycles. Without the telecentric in object space properties of the inspection system 100, the detected signal and noise patterns would vary with the position of the light beam. This would be the case, for example, if multiple the detectors were to be placed in a space above the inspected specimen.

By using a Fourier transform lens, the lens system 100 is relatively insensitive to focus at the collection end, in spite of the very high collection NA. The Fourier lens maps scattering angles leaving the wafer into position in the Fourier plane. Objects scattering light at a particular angle that are defocused from the nominal focus position will still scatter in the same angle and the light will reach the Fourier plane in the same location. The angle of incidence at the Fourier plane may change slightly, but this does not affect the mapping function. The inspection system 100 is relatively insensitive to maintaining a focus on the wafer 102 because the Fourier forming lenses 104 are relatively focus insensitive. This means that the distance between the wafer 102 and the inspection system 100 has relatively little effect on the point upon which scattered light rays impinge upon the Fourier plane 120. The focus insensitivity of the inspection system 100 obviates the need for complex auto-focusing mechanisms required to keep the wafer at the right focal position. The Fourier forming lenses 104 provide the extra cost benefit that the lenses are simple, thereby eliminating the need for high quality lenses.

The image at the Fourier plane 120 is detected by placing a detector device 110 at the Fourier plane 120. The detector device 110 includes many individual and adjacent detectors that detect the scattered light rays associated with each of the angles at which light scattered from wafer 102. The detector device 110 can be a variety of detectors ranging from micro-channel plate, a hybrid photo-multiplier (PMT), a charge couple device (CCD) camera, an array of photo-diode arrays, optical fibers, CMOS detector arrays, or other spatial resolving detectors.

A micro-channel plate, as is commonly known in the art, is an array of photo-multipliers, each able to detect light signals. Micro-channel plates have typical array sizes of 10×10 to 16×16 that can be placed in the Fourier plane 120 to detect the scattered of light. CCD cameras, which can have thousands of pixels, can be used even though only a few thousand detectors are sufficient for use in the present invention. Optical fibers can be used by placing fibers at the Fourier plane 120 and connecting their opposite ends to a device capable of processing the collected signals. Addressable PMTs are useful in that they can be individually controlled such that maximum signal-to-noise ratios can be obtained. For instance, only selected detectors in an array of detectors need be activated to obtain a high signal-to-noise image. In general, the ability to be selective as to the detectors in the Fourier plane allows for Fourier filtering methods. For example, the PMT channels can be time gated.

Figure 2:
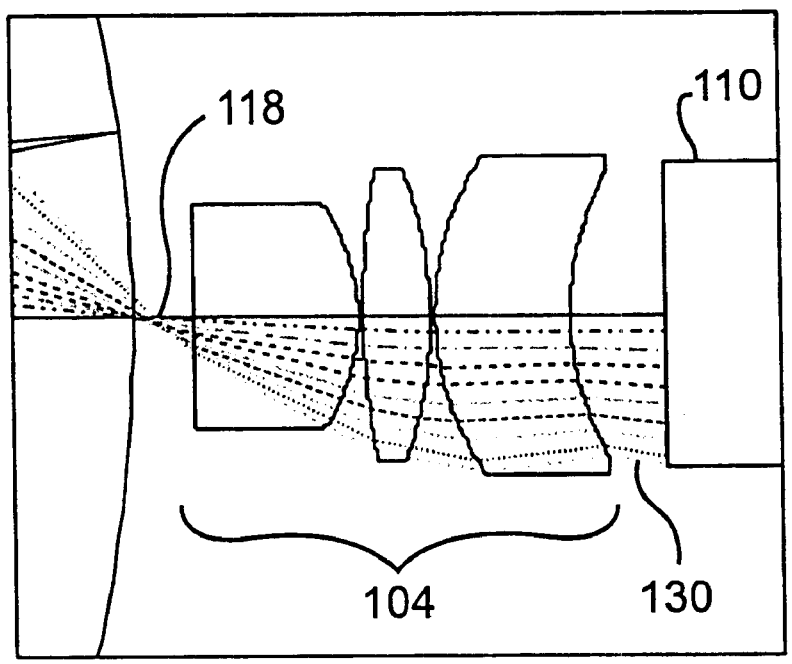
FIG. 2 illustrates a side plane, enlarged view of the Fourier forming lenses that exhibit Fourier plane mapping characteristics.

FIG. 2 illustrates a side plan, enlarged view of the Fourier forming lenses 104 that exhibit desirable Fourier plane mapping characteristics. Fourier plane mapping characteristics refers to the fact that the scattered light rays 130 from the wafer which are illustrated in equal angle increments (10, 20, 30, 40, 50, 60, 70, 80 and 85 degrees) exit the lenses 104 such that they are substantially equally spaced apart as they impinge the detector 110. This is to say that the mapping of the scattering angle at the wafer, $\theta$ as measured from the surface normal, to the Fourier plane location (y) is mapped as y=(system focal length)* $\theta$, rather than the normal mapping of y=(system focal length)* $\sin(\theta)$. Without this optimized Fourier plane mapping, the scattered light rays that come off of the wafer 102 at large $\theta$ are more difficult to detect since it becomes physically difficult to place light detectors in decreasing space constraints. On the other hand, Fourier plane mapping converts the relationship such that y is proportional to $\theta$, rather than $\sin(\theta)$. Therefore, Fourier plane mapping allows for detectors to be equally spaced apart, which is more physically practical. Adding the Fourier plane mapping characteristics to the Fourier forming lenses 104 is an optional feature of the present invention. However, it is a preferable to utilize optimized Fourier plane mapping.

Alternative embodiments of the inspection system 100 utilize the Fourier forming lenses with similar function to lenses 104, but do not utilize the hemispherical mirror 106. These embodiments can take advantage of the image capabilities at the Fourier plane, but with a smaller collection angle of light scattered from the wafer.

Figure 3:
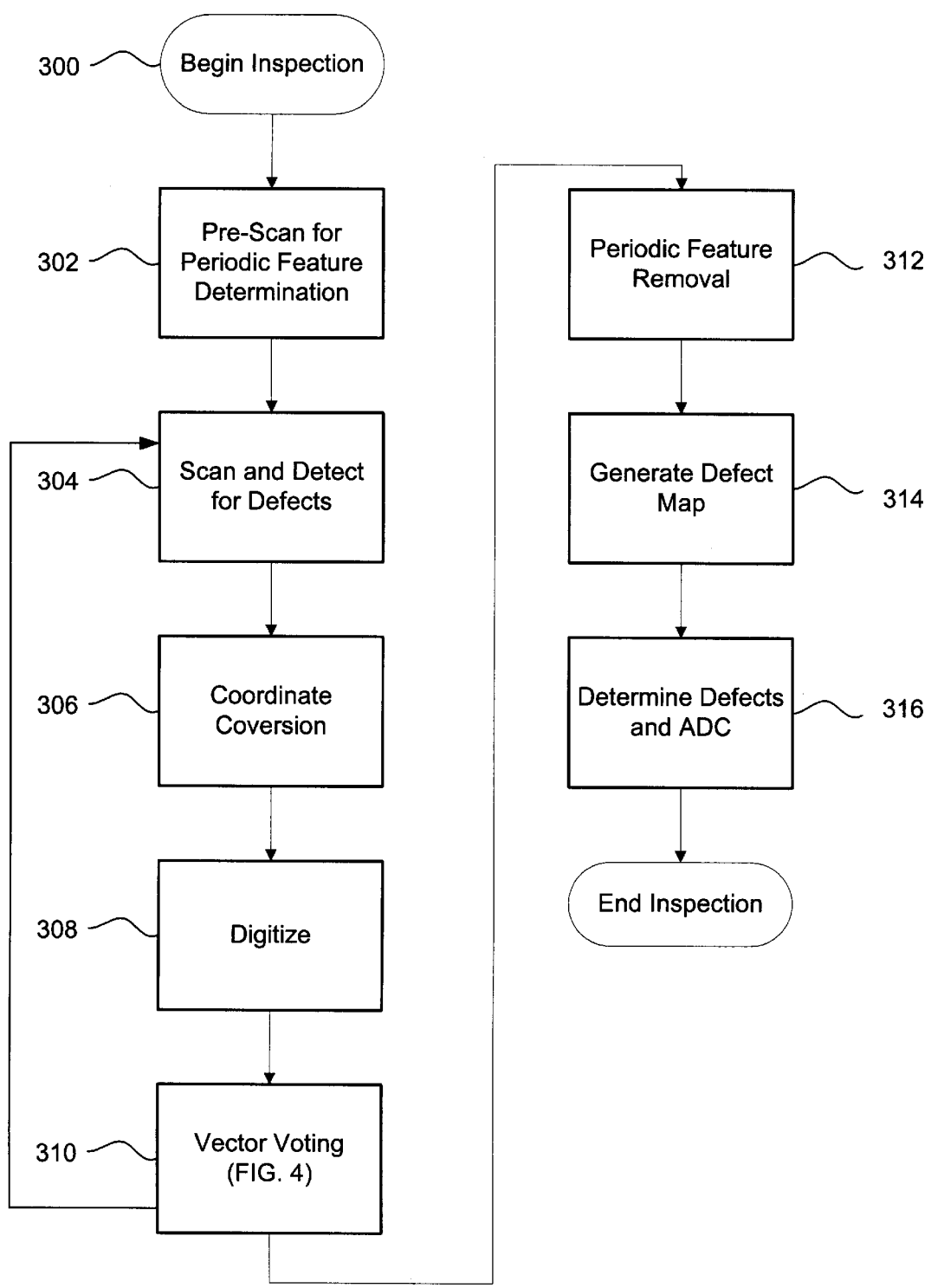
FIG. 3 illustrates one method of performing a process for obtaining defect information using the inspection system of the present invention.

The methods for using the inspection system 100 and processing the collected signals for defect detection will now be described through flow diagrams in FIGS. 3 and 4. FIG. 3 illustrates one method of performing a process for obtaining defect information using the inspection system of the present invention. The process of obtaining defect information 300 begins in block 302 by scanning at least a portion of the specimen to determine the distribution of light scattered from the structures on a semiconductor wafer. In some wafers, the structures are formed in a regularly repeating pattern. For example, an entire semiconductor wafer can be patterned such that it contains many individual device areas having the same circuitry layout. For example, each device area may have DRAM circuitry for memory and dense logic circuitry for micro-processing. In DRAM areas, the wafer structure is periodic and light will scatter off each of these device areas in a similar manner, the collected signals are not directly useful for the identification of defects. Ultimately, the useful information will be light scattered from defects on the specimen. Therefore, light from the wafer's structures is labeled as noise. By scanning the specimen for structure scattering data, or noise, it is possible later in the inspection process to differentiate or remove the noise from the defect signals. A portion or the entire specimen can be scanned to determine the light scattering distributions. However, it is more efficient to only scan a portion of the specimens.

Referring to block 304, after obtaining a sufficient amount of scanned data in order to determine the distribution of light scattered from the wafer structures, the specimen is scanned for defects. As mentioned above, this is performed by moving the inspection system and the specimen relative to each other such that the surface of the specimen of interest is covered. If the specimen is scanned in a spiral pattern, the data can be converted into the Cartesian coordinate system in block 306 for simpler computations of defect location relative to the die structure on the wafer.

In block 308, the analog signals collected from the detectors can optionally be converted into digital signals.

In block 310 each image of scattered light collected is processed such that the signals for the defects are emphasized over the noise created by the periodic structures. This processing, which is referred to as vector voting, identifies the locations in the Fourier plane where the signal-to-noise ratio is high so that defect analysis becomes more accurate. Different types of defects have their own characteristic distribution in which light scatters from the surface of a specimen. Vector voting takes advantage of this phenomenon and allows the inspection system to be "tuned" to detect each of a various number of defect types. Through this capability, the inspection system of the present invention is capable to differentiate between defect types and thereby provide a classification of the defects present on a specimen. More detailed description relating to vector voting will be described in FIG. 4.

Figure 5A:
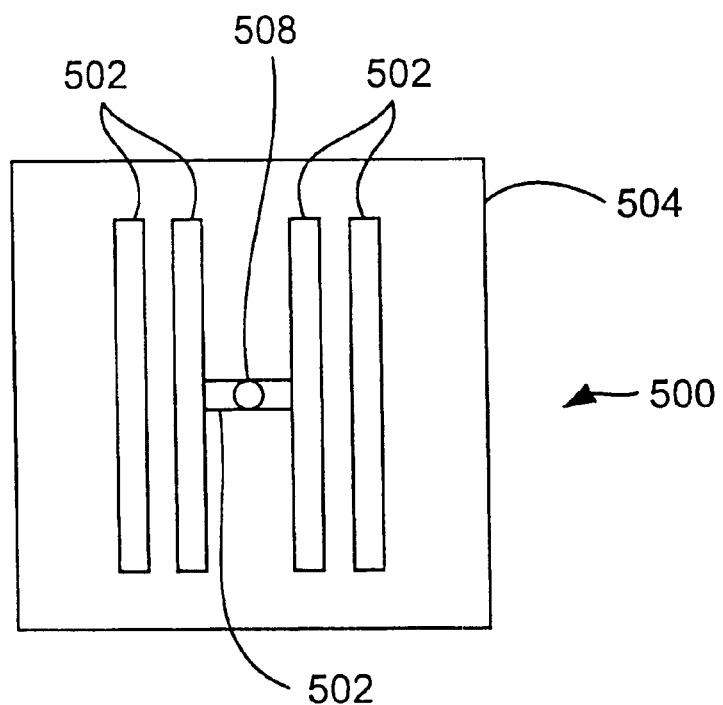
FIGS. 5(a) and 5(b) illustrate top plan and side plan views, respectively, of structures on a small portion of a semiconductor wafer.
Figure 5B:
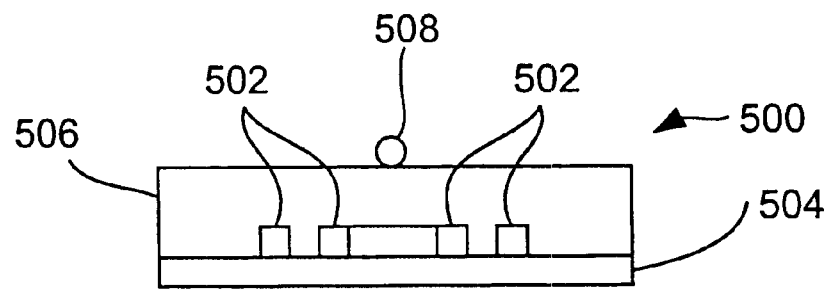
Figure 6:
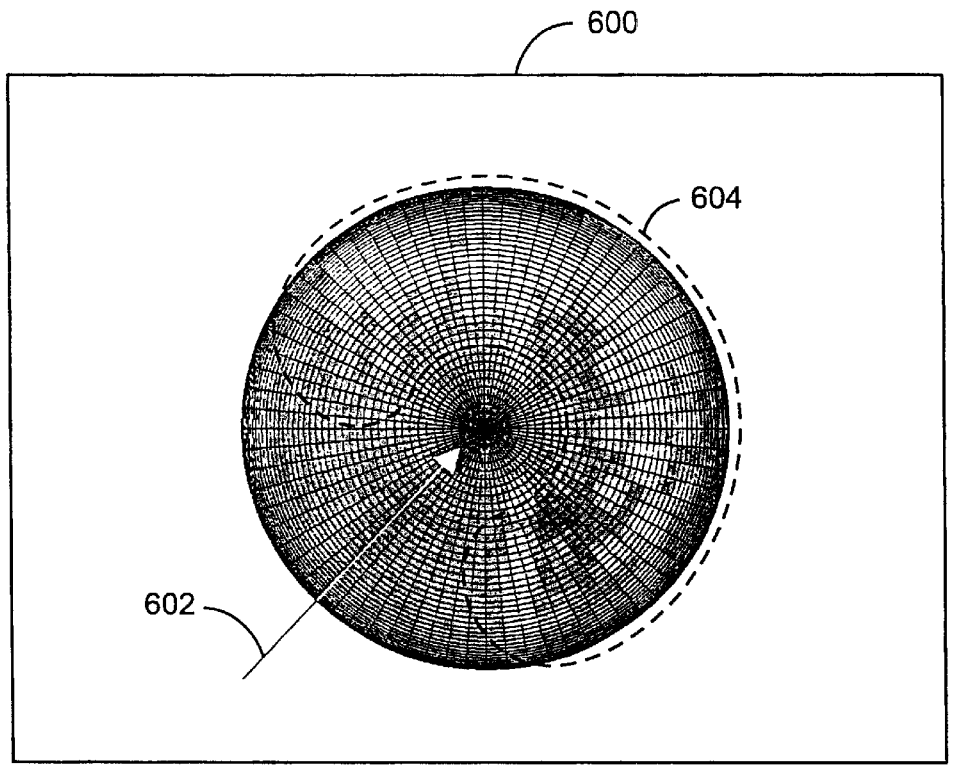
FIG. 6 illustrates the distribution over the hemisphere of light that scatters off the wafer of FIGS. 5(a) and 5(b) when no defect is present; the noise distribution.
Figure 7:
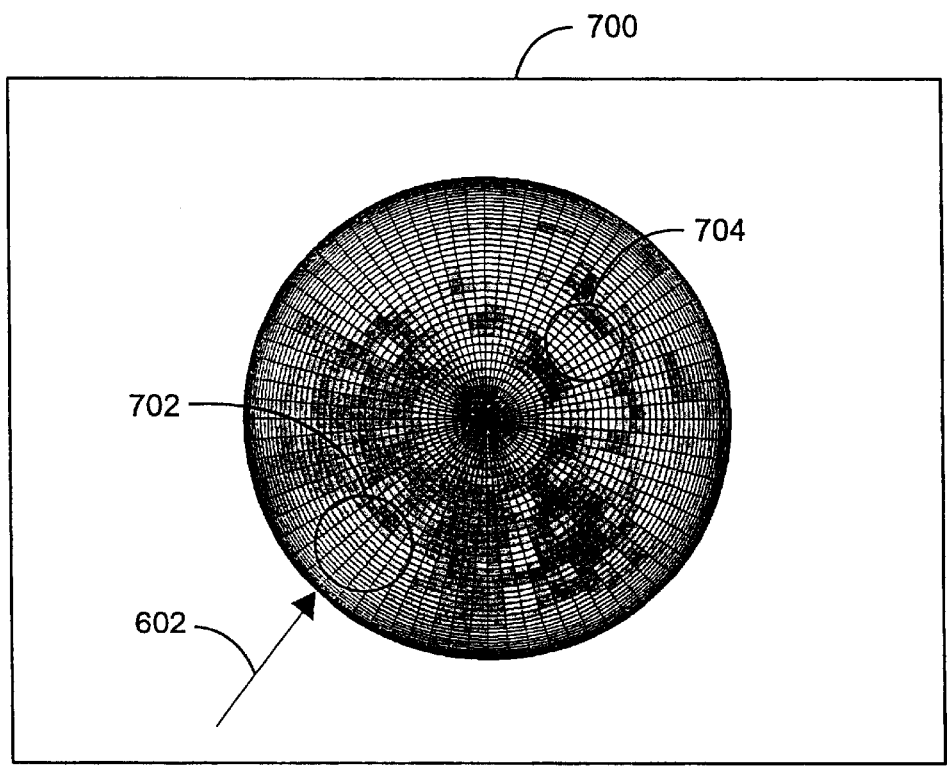
FIG. 7 represents the hemispherical distribution for the same periodic structures in FIGS. 5(a) and 5(b) when a defect is present.

In block 312, the signal-to-noise ratio is increased further by removing the noise pattern determined from operation 302. To further explain the process for removing noise from the collected image, FIGS. 5(a) and 5(b), FIG. 6 and FIG. 7 are now presented. FIGS. 5(a) and 5(b) illustrate top plan and side plan views, respectively, of a structure on a portion of a semiconductor wafer 500. The line structures 502 are formed on a metal layer 504 and are embedded within a layer of $SiO_2$ 506. A defect 508, for example a foreign particle, is on the surface of the wafer 500. FIG. 6 illustrates the image distribution 600 of light that scatters off wafer 500 in FIGS. 5(a) and 5(b) when no defect is present; the noise distribution. Image 600 is presented on a hemispherical coordinate system representing the hemisphere into which light scatters when reflected off the wafer 500. The direction of the incident light source, shown by line 602, causes light to reflect off the wafer 500 into the upper-right portion of the hemisphere, as shown by the light portions 604. FIG. 7 represents the image distribution 700 for the same periodic structures in FIGS. 5(a) and 5(b) when defect 508 is present. The image distribution 700 is similar to the image distribution 600 except for additional areas of reflected light 702 and 704. Areas 702 and 704 represent the locations outside of the noise into which light rays scatter from defect 508. Since these areas 702 and 704 are outside of the noisy area 604, these areas have high defect signal values. It is noted that the areas into which light is scattered from defects is usually very small in comparison to the periodic light scattering distributions. Operation 312, of removing noise from the collected signals, results in a high signal-to-noise image useful for defect detection.

Referring back to FIG. 3, operational block 314 creates a defect map of the entire area of interest on a specimen by combining the images for the various discrete areas scanned by the inspection system. Finally, by utilizing the defect map in operation 316, it is possible to then determine the defects present on a specimen and classify the types of defects. Defect classification is possible because certain defect types have scatter distributions that are characteristic to the defect type.

Generally, one method for determining the presence of defects is to multiply the signal grabbed at a sample in time by a matrix, and then summing the multiplied intensity values for each sample. A defect is determined to exist if the sum is different than a predetermined value.

It should be noted that after the pre-scanning is completed in block 310, blocks 304 through 310 are iterated for each sample or area on a semiconductor wafer to be inspected. During each iteration, a new area on the wafer is inspected and vector voting is performed. The locations of any defects identified through vector voting during each iteration are immediately recorded. After the iterations of blocks 304 through 310 are complete, defects that appear to be periodic on a distance corresponding to the die size on the wafer should be eliminated from the list of identified defects as they are most likely associated with the wafer's structure and not an isolated defect. FIG. 3 shows that coordinate conversion and digitization are performed during each iteration. In alternative embodiments, the coordinate conversion and digitization of blocks 306 and 308 can be performed after the iterations of blocks 304 through 310 have been completed.

Figure 4:
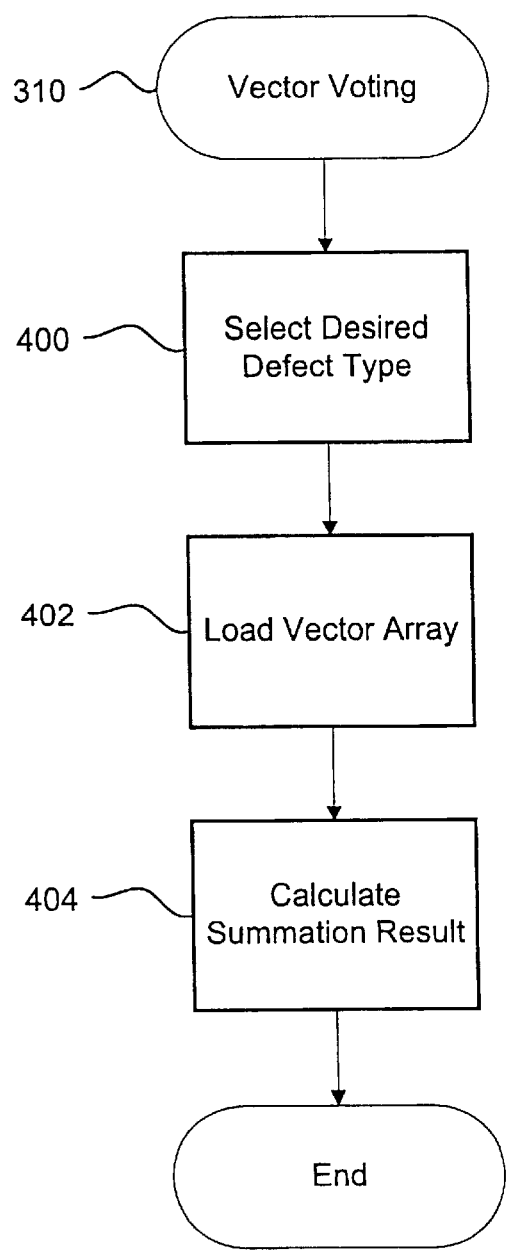
FIG. 4 illustrates the individual operations of the vector voting operation of FIG. 3.

FIG. 4 illustrates the individual operations of the vector voting operation 310 of FIG. Vector voting begins with operation 400 where the type of defect to be detected is determined. It is noted that each type of defect usually has a characteristic light scattering distribution. By tailoring the signal enhancing processes in accordance to the type of defects expected on a specimen, the inspection system of the present invention can be tuned to detect specific defect types.

In block 402, vector values associated with certain defect types are loaded into a column array. Each of the vectors is a factor by which the Fourier plane intensity value for each of the sub-areas of a scanned portion on the wafer will be multiplied. The array of vector values will increase the intensity values associated with the sub-areas in which defect signals are expected and will decrease intensity values associated with the sub-areas in which mostly noise is expected. Vector values tailored to specific defect types magnify and minimize signal values depending upon the locations into which high defect signals are expected. For example, with respect to FIG. 7, the vectors for areas 702 and 704 will increase signal values and vectors for the areas outside of 702 and 704 will decrease signal values. Ultimately, the defect information obtained is more discerning as to the presence of defects. In an alternative embodiment, the reverse approach to vector values can be taken where vector array values can be set so that intensity values likely to be associated with defect signals are increased and intensity values likely to be associated with noise are decreased. In this alternative embodiment, defects are identified when the sum of the multiplied intensity signals are generally low in value, rather than when they are high.

In block 404, the summation result of the collected signal values multiplied by the vector values is obtained. As described above, in certain algorithms, a defect is determined to exist when the summation result of the signal intensity values multiplied by the vector values is greater, less than, or different than a specific value. Again it is noted that the identification of defects can be accomplished through various mathematical algorithms other than the method of obtaining a summation result.

Vector voting can be performed for multiple defect types during an inspection cycle. For example, this is accomplished by using different arrays of vector values for each type of defect to be detected. In alternative embodiments of the inventive method, vector voting can be implemented without the operations of removing periodic feature scattering distributions.

Figure 8:
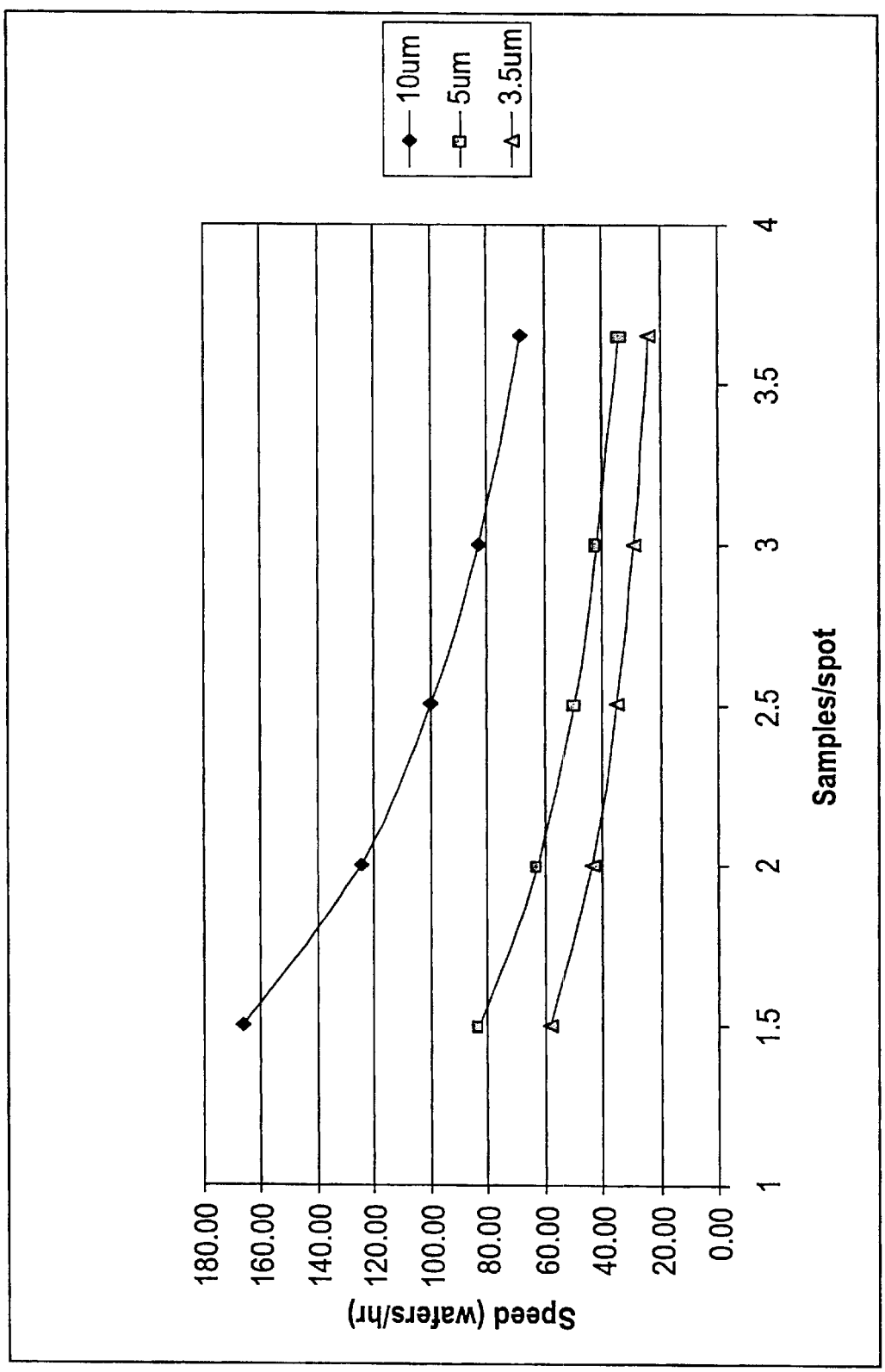
FIG. 8 illustrates a graph of the inspection speed, in wafers per hour, versus the number of pixels per scanning spot for an inspection system having a field of view of 2 mm.

FIG. 8 illustrates a calculation of the inspection speed, in wafers per hour, versus the number of samples of intensity from the Fourier plane detector 110 per scanning spot for an inspection system having a field of view of 2 mm. The speed of inspection increases as the number of samples per spot decreases since less data calculation is required. Three relationships are illustrated for three scanning spot sizes: the diamond curve for a 10 um spot size, a square curve for a 5 um spot size, and a triangle curve for a 3.5 um spot size. The high speeds obtained by the inspection system of the present invention are contributed to the telecentric properties that allow for scanning of the light source over the wafers.

While this invention has been described in terms of several preferred embodiments, there are alteration, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

I claim:

1. An optical inspection system for inspecting a specimen comprising:
    a light source for transmitting a light beam to be incident upon the surface of the specimen, the light beam causing light rays to scatter from the surface of the specimen;
    a set of optical lenses positioned to receive the light rays scattering from the specimen and configured to transmit the scattered light rays into a Fourier plane, whereby a Fourier transform of the specimen is created at the Fourier plane; and
    a plurality of detectors placed in the Fourier plane to detect the scattered light rays, wherein each of the detectors are individually addressable so that selected ones of the plurality of detectors can be utilized to perform Fourier filtering, whereby the features of the specimen can be determined from the collected scattered light rays.

2. An optical inspection system as recited in claim 1 wherein each of the plurality of detectors are photomultipliers set within a micro-channel plate.

3. An optical inspection system as recited in claim 1 wherein the set of optical lenses are configured to direct the scattered light rays such that the light rays are equally spaced apart at the Fourier plane, wherein the position of each light ray in the Fourier plane is proportional to the scattering angle at the specimen of each respective light ray.

4. An optical inspection system as recited in claim 1 further comprising:
   an optical plate element having a bottom surface that has a transparent region and a reflective region, the optical plate element placed over an area of the specimen to be inspected; and
   a substantially hemispherical mirror placed above the transparent plate to collect and then direct the scattered light from the specimen towards the set of optical lenses.

5. An optical inspection system for analyzing a specimen comprising:
   a light source for transmitting a light beam to be incident upon the surface of the specimen, the light beam causing light rays to scatter from the surface of the specimen;
   a set of optical lenses positioned to receive the light rays scattering from the specimen and configured to transmit the scattered light rays into a Fourier plane, whereby a Fourier transform of the specimen in created at the Fourier plane;
   a plurality of detectors placed in the Fourier plane to detect the scattered light rays, whereby an image of the specimen can be created; and
   a substantially hemispherical mirror placed over an area of the specimen to be inspected, wherein the mirror is configured to collect and then direct the scattered light rays from the specimen towards the set of optical lenses.

6. An optical inspection system as recited in claim 5 wherein the set of optical lenses cause the spatial separation of each of the light rays at the Fourier plane to be directly proportional to the angle at which the respective light rays emanate from the specimen.

7. An optical inspection system as recited in claim 5 wherein each of the plurality of detectors are individually addressable such that only detectors that collect high defect signal light rays scattered from the specimen are activated.

8. An optical inspection system as recited in claim 5 wherein each of the detectors are individually addressable so that selected ones of the plurality of detectors can be utilized to perform Fourier filtering.

9. An optical inspection system as recited in claim 5 wherein each of the plurality of detectors are photo-multipliers set within a micro-channel plate.

10. An optical inspection system as recited in claim 5 wherein each of the plurality of detectors are a type selected from the group consisting of a charge couple device camera, an optical fiber detector system, and an array of photo-diode arrays.

11. An optical inspection system as recited in claim 5 that is telecentric in object space.

12. An optical inspection system as recited in claim 11 further comprising a field of view over which the light beam can be scanned, whereby the scanning of the light beam increases the inspection speed of the optical inspection system.

13. An optical inspection system as recited in claim 5 further comprising:
   an optical plate element having a bottom surface that has a transparent region and a reflective region, the optical plate element placed over an area of the specimen to be inspected and underneath the hemispherical mirror.

14. A method of detecting defects on a material specimen using an optical inspection system comprising:
   irradiating a spot on the specimen with a light source, the light source causing light rays to scatter from the surface of the specimen;
   detecting an image of the scattered light rays at a Fourier plane, the Fourier plane created by a set of Fourier plane forming lenses within the optical inspection system;
   multiplying a signal value for each discrete portion of the irradiated spot by a respective vector value to obtain a respective adjusted signal value;
   evaluating a sum total of the respective adjusted signal values for the irradiated spot; and
   determining a defect exists if the sum total of the respective adjusted signal values for the irradiated spot is different than a predetermined value.

15. A method as recited in claim 14 wherein the each of the vector values cause a respective signal value to increase if associated with a defect signal, and wherein each of the respective vector values cause a respective signal value to decrease if associated with a noise signal.

16. A method as recited in claim 14 wherein the each of the vector values cause a respective signal value to decrease if associated with a defect signal, and wherein each of the respective vector values cause a respective signal value to increase if associated with a noise signal.

17. A method as recited in claim 14 wherein a defect is determined to exist when it is determined that the sum total of the respective adjusted signal values for the irradiated spot is greater than a predetermined value.

18. A method as recited in claim 14 wherein a defect is determined to exist when it is determined that the sum total of the respective adjusted signal values for the irradiated spot is less than a predetermined value.

19. A method as recited in claim 14 wherein the respective vector values are selected based upon a specific type of defect that is intended to be detected on the specimen.

20. A method for detecting defects on a material specimen wherein the operations of claim 14 are repeated and wherein the irradiating spot is scanned over a portion of the specimen within a field of view of the inspection system.

21. A method as recited in claim 20 further comprising:
   creating a defect map for the specimen utilizing the respective sum totals for each irradiated spot on the specimen.

22. A method as recited in claim 20 wherein the light beam is telecentric in object space within the field of view.

23. A method as recited in claim 14 further comprising:
   scanning at least a portion of the specimen with the light source to obtain a structure image, which is an image of the scattered light rays caused by structures on the specimen; and
   subtracting the periodic image from the defect map to obtain a resulting defect map, whereby the resulting defect map has a high signal-to-noise ratio.

* * * * *

UNITED STATES PATENT AND TRADEMARK OFFICE
CERTIFICATE OF CORRECTION

PATENT NO. : 6,603,541 B2
DATED : August 5, 2003
INVENTOR(S) : Steven R. Lange

It is certified that error appears in the above-identified patent and that said Letters Patent is hereby corrected as shown below:

<u>Title page, Item [54] and Column 1, lines 1 and 2,</u>
Change "WAFER INSPECTION USING OPTIMIZED GEOMETRY" to
-- WAFER INSPECTION USING OPTIMIZED COLLECTION GEOMETRY --.

Signed and Sealed this

Seventeenth Day of February, 2004

JON W. DUDAS
*Acting Director of the United States Patent and Trademark Office*